United States Patent
Potdar et al.

(10) Patent No.: US 12,296,153 B2
(45) Date of Patent: May 13, 2025

(54) METHOD OF SEALING A SYRINGE BARREL

(71) Applicant: KAIRISH INNOTECH PRIVATE LIMITED, Maharashtra (IN)

(72) Inventors: Pratul Prakash Potdar, Nani Daman (IN); Anil Narayan Narvekar, Goa (IN)

(73) Assignee: Kairish Innotech Private Limited, Mumbai (IN)

( * ) Notice: Subject to any disclaimer, the term of this patent is extended or adjusted under 35 U.S.C. 154(b) by 20 days.

(21) Appl. No.: 17/967,482

(22) Filed: Oct. 17, 2022

(65) Prior Publication Data

US 2023/0049720 A1    Feb. 16, 2023

Related U.S. Application Data

(62) Division of application No. 15/939,135, filed on Mar. 28, 2018, now abandoned.

(30) Foreign Application Priority Data

Mar. 31, 2017    (IN) .............................. 201721011597

(51) Int. Cl.
*A61M 5/32*    (2006.01)
*A61M 5/24*    (2006.01)
(Continued)

(52) U.S. Cl.
CPC ............ *A61M 5/3202* (2013.01); *A61M 5/24* (2013.01); *A61M 5/3134* (2013.01);
(Continued)

(58) Field of Classification Search
CPC .............. A61M 5/3202; A61M 5/3134; A61M 5/5086; A61M 5/24; A61M 2005/3104;
(Continued)

(56) References Cited

U.S. PATENT DOCUMENTS 4,733,787 A * 3/1988 Knopf ................... B65D 51/18
                                                       215/254
4,758,230 A   7/1988 Rycroft
(Continued)

FOREIGN PATENT DOCUMENTS

DE    102014111944 A1    3/2016
EM    002911958-0001     12/2015

OTHER PUBLICATIONS

Vetter Packaging Solutions, brochure, pp. 1-12, 2015.

*Primary Examiner* — Joel M Attey
*Assistant Examiner* — Antarius S Daniel
(74) *Attorney, Agent, or Firm* — Renner, Otto, Boisselle & Sklar, LLP

(57) ABSTRACT

Disclosed is a method of sealing a syringe barrel having a syringe tip with a collar. The syringe tip is sealed with a resilient closure. A tamper evident syringe tip cap comprising a cap member and a sleeve member separated by an annular first breaking line is then pushed over the resilient closure, to couple the proximal end of the sleeve member with the collar. The distal end of the resilient closure is accommodated in the cap member and protrudes beyond the sleeve member. The first breaking line is bridged by a coupling strip. For use of the syringe and providing access to the closure, the first breaking line is broken by pivoting the cap member away. The sleeve member remains coupled to the collar. Further tearing the cap member downward causes breaking a second breaking line provided in the sleeve member, thereby enabling removing the entire syringe tip cap.

14 Claims, 11 Drawing Sheets

(51) Int. Cl.
*A61M 5/31* (2006.01)
*A61M 5/50* (2006.01)
*A61J 1/14* (2023.01)
*A61M 5/34* (2006.01)

(52) U.S. Cl.
CPC .......... *A61M 5/5086* (2013.01); *A61J 1/1412* (2013.01); *A61M 5/2466* (2013.01); *A61M 2005/3104* (2013.01); *A61M 2005/312* (2013.01); *A61M 5/347* (2013.01); *A61M 2005/5073* (2013.01); *A61M 2207/00* (2013.01)

(58) Field of Classification Search
CPC .... A61M 2005/3103; A61M 2005/312; A61M 2005/5073; A61J 1/1412; B65D 43/00; B65D 43/0225; B65D 43/02; B65D 47/00
See application file for complete search history.

(56) References Cited

U.S. PATENT DOCUMENTS

| | | | |
|---|---|---|---|
| 5,165,560 A * | 11/1992 | Ennis, III | B65D 51/002 |
| | | | 215/274 |
| 5,344,404 A | 9/1994 | Benson | |
| 5,496,288 A | 3/1996 | Sweeney | |
| D417,275 S | 11/1999 | Conforti | |
| D419,671 S | 1/2000 | Jansen | |
| D431,864 S | 10/2000 | Jansen | |
| 6,190,364 B1 | 2/2001 | Imbert | |
| 6,196,998 B1 | 3/2001 | Jansen et al. | |
| D447,797 S | 9/2001 | Odell et al. | |
| D447,799 S | 9/2001 | Jun | |
| 6,520,935 B1 | 2/2003 | Jansen et al. | |
| D544,600 S | 6/2007 | Wentling | |
| D557,414 S | 12/2007 | Wentling | |
| 7,367,964 B2 | 5/2008 | Heinz et al. | |
| 7,648,481 B2 | 1/2010 | Geiger et al. | |
| 8,235,951 B2 | 8/2012 | Hund et al. | |
| D713,029 S | 9/2014 | Shiraishi et al. | |
| 8,920,369 B2 | 12/2014 | Salahieh et al. | |
| 9,039,676 B2 | 5/2015 | Klima | |
| 9,095,667 B2 | 8/2015 | Von Schuckmann | |
| 9,604,012 B2 | 3/2017 | Horita et al. | |
| D787,052 S | 5/2017 | Heinz et al. | |
| D788,296 S | 5/2017 | Ishida et al. | |
| 9,649,449 B2 | 5/2017 | Glocker | |
| 9,694,948 B1 | 7/2017 | Pakhomov et al. | |
| D800,587 S | 10/2017 | Cho et al. | |
| D802,760 S | 11/2017 | Neby | |
| D838,363 S | 1/2019 | Katagiri et al. | |
| 2008/0097310 A1 | 4/2008 | Buehler et al. | |
| 2009/0283493 A1* | 11/2009 | Witowski | A61M 5/5086 |
| | | | 215/258 |
| 2011/0000871 A1 | 1/2011 | Bernard et al. | |
| 2011/0015578 A1* | 1/2011 | Lowke | A61M 5/5086 |
| | | | 604/403 |
| 2012/0123334 A1 | 5/2012 | Schraga | |
| 2013/0043206 A1* | 2/2013 | Ochoa Laburu | B65D 47/0814 |
| | | | 215/237 |
| 2013/0338575 A1 | 12/2013 | Glocker et al. | |
| 2013/0338603 A1 | 12/2013 | Roedle et al. | |
| 2013/0338604 A1 | 12/2013 | Roedle | |
| 2014/0158700 A1 | 6/2014 | Glocker et al. | |
| 2015/0238703 A1* | 8/2015 | Glocker | A61M 5/347 |
| | | | 604/198 |
| 2015/0246184 A1 | 9/2015 | Hund et al. | |
| 2015/0343155 A1 | 12/2015 | Zenker et al. | |
| 2016/0022925 A1 | 1/2016 | Zenker | |
| 2016/0101914 A1* | 4/2016 | Logel | B65D 51/244 |
| | | | 220/214 |

\* cited by examiner

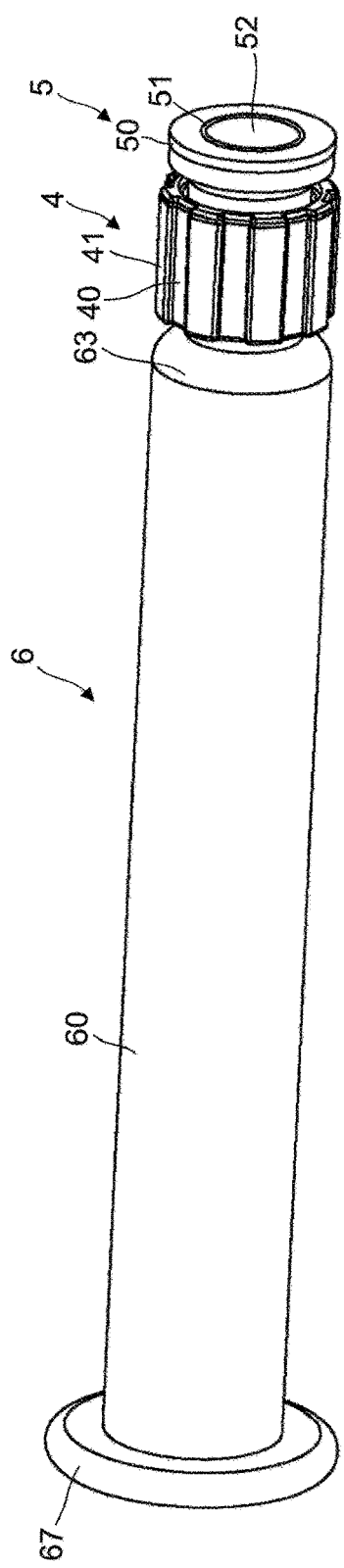
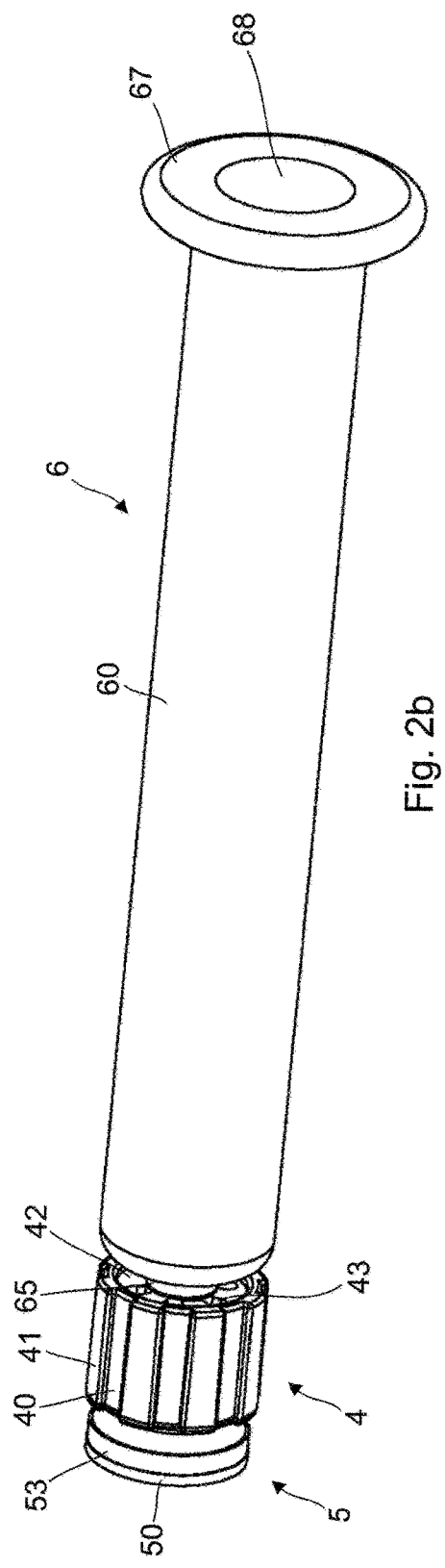
Fig. 2a
Fig. 2b

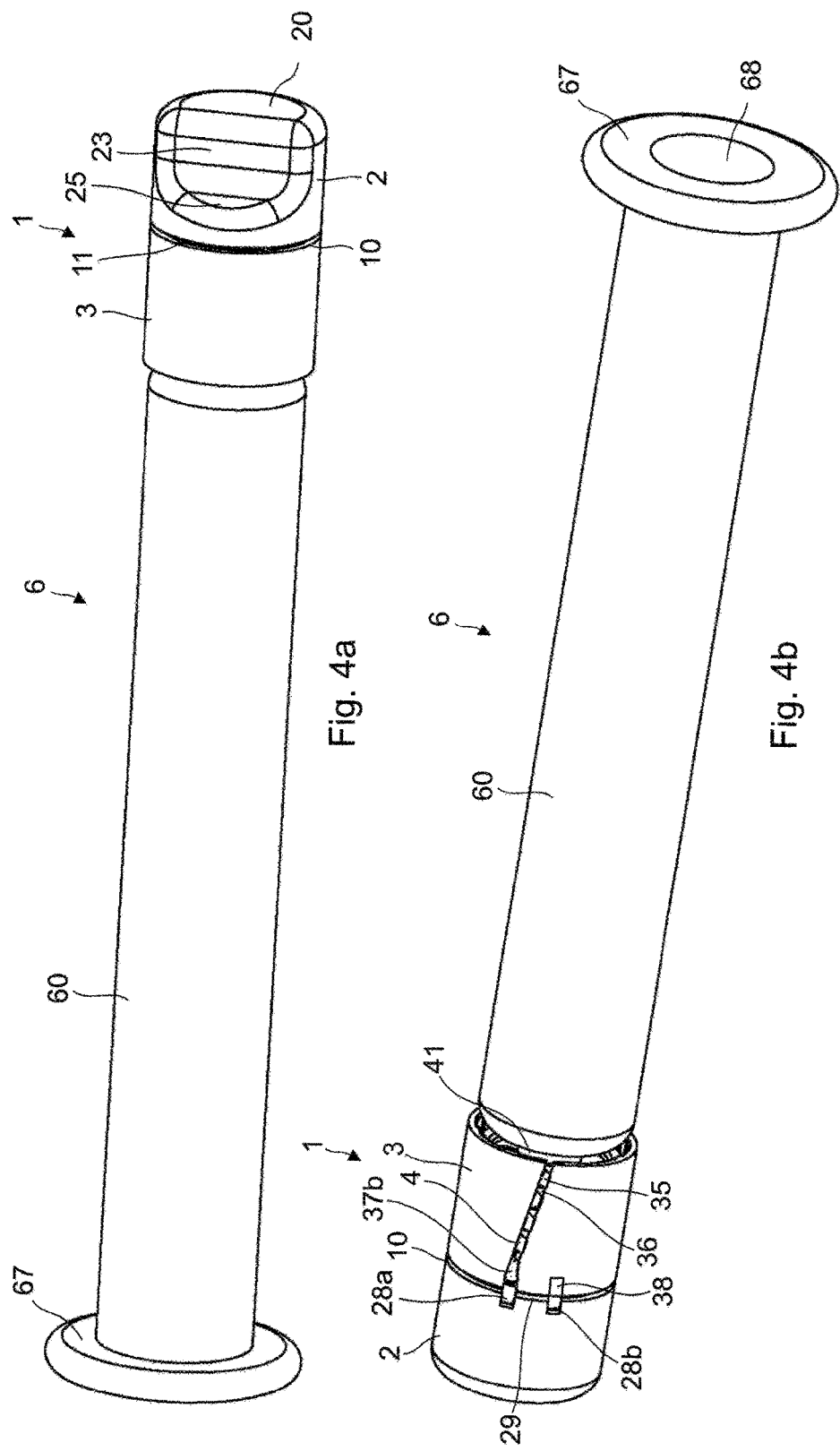

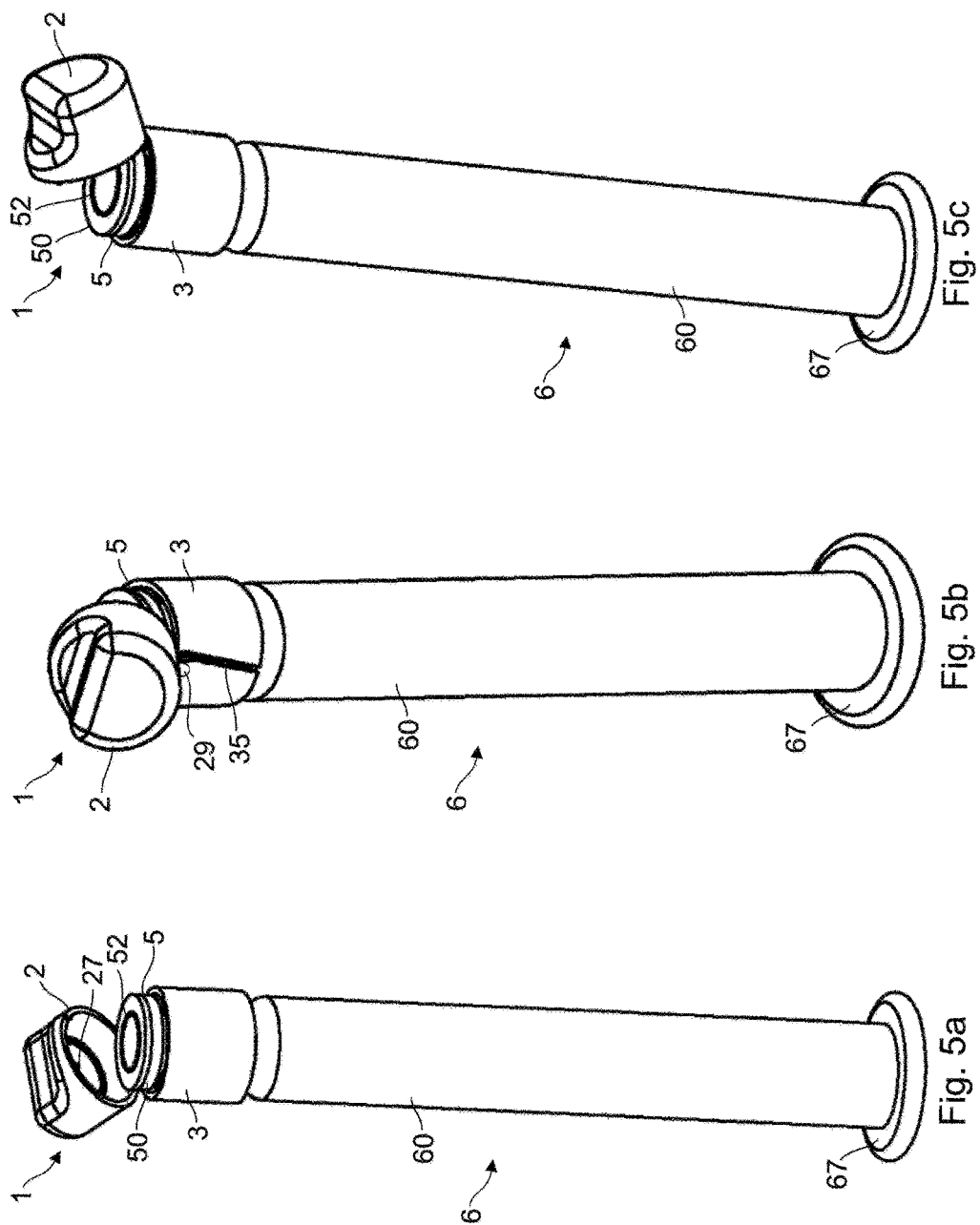

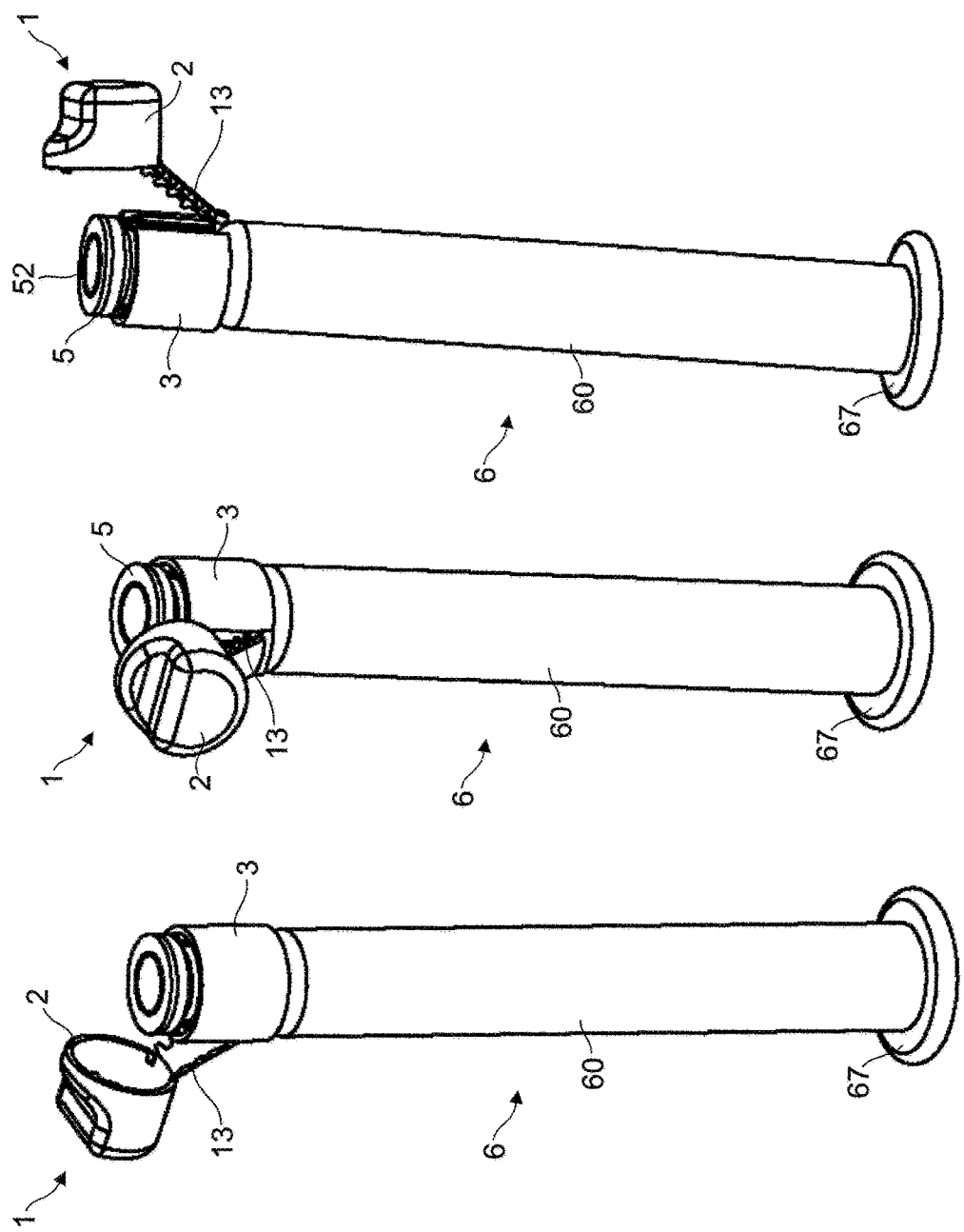

METHOD OF SEALING A SYRINGE BARREL

CROSS REFERENCE TO RELATED APPLICATIONS

The present application claims benefit of and priority under 35 U.S.C. § 120 to co-pending U.S. application Ser. No. 15/939,135, filed 28 Mar. 2018, which in turn claims priority under 35 U.S.C. § 119 of India patent application no. 201721011597 'Syringe Tip Cap Assembly, Syringe Comprising such a Syringe Tip Cap and Method of Sealing a Syringe Barrel', filed on 31 Mar. 2017, the whole content of each of which is hereby incorporated by reference.

FIELD OF THE INVENTION

The present invention generally relates to drug delivery devices and containers, and more specifically relates to a syringe tip cap assembly for securely sealing the tip of a syringe barrel, as well as a syringe and a method of sealing such a syringe with a resilient closure and a syringe tip cap.

BACKGROUND OF THE INVENTION

Conventional syringes, which are typically made of plastic or preferably of glass, comprise a barrel having an open proximal end and an opposite distal end. A cylindrical wall extends between the ends, which defines a substance retaining chamber. An elongate syringe tip projects from the distal end of the syringe barrel and includes a narrow passage which communicates with the substance retaining chamber of the barrel. A plunger may be inserted into the open proximal end of the syringe barrel for sliding fluid-tight engagement with the cylindrical chamber wall. Sliding movement of the plunger in a distal direction urges fluid in the chamber through the passage in the tip for administering the substance. Conversely, sliding movement of the plunger in a proximal direction draws fluid through the passage in the tip and into the chamber of the syringe barrel.

Such syringes may further include a needle assembly with a needle cannula having a proximal end, a pointed distal end and a lumen extending axially therethrough. The needle assembly also includes a hub which is engageable with mounting means on the syringe barrel for selectively placing the lumen of the needle cannula in fluid communication with the passage through the tip of the syringe barrel. Such a mounting means may be a luer collar disposed in spaced concentric relationship around the tip of the syringe barrel. The luer collar includes an array of threads for threaded engagement with corresponding structure on the hub of the needle. For example, the luer collar may include an array of internal threads which are engageable with projections extending outwardly from the hub of the needle cannula. Syringe barrels formed from plastic may have the luer collar unitarily molded therewith. However, glass syringe barrels may not be easily formed with an integral luer collar. Thus, glass syringe barrels and some plastic syringe barrels may have a separately formed luer collar securely mounted to the tip of the syringe barrel. The luer collar may rely upon a slip fit interengagement, a snap fit or other such secure mounting engagement around the tip of the syringe barrel.

Medications that are pre-filled into a syringe barrel must be sealed to prevent contamination or loss of the medication. For this purpose, stoppers or closures of an elastomeric material are mounted over the tip at the distal end of the syringe barrel to prevent leakage and to avoid contamination of the medication. Tip caps according to the prior art have been formed from elastomeric material frictionally and/or resiliently retained in engagement with the tip of the syringe barrel and can be removed from the syringe tip shortly prior to usage of the syringe. The hub of the needle assembly may then be securely engaged with the luer collar or other mounting means adjacent the exposed tip of the syringe barrel. For example, the needle hub may be threadedly engaged within the luer collar such that the lumen of the prior needle cannula communicates with the exposed tip of the syringe barrel.

Such seals must be reliably held on the syringe tip, for sealing the syringe tip over an extended period of time. For this purpose, syringe tip caps are used, which retain the seals in axial direction and are configured to provide evidence of tampering or misuse of a pre-filled syringe.

One such syringe tip cap is disclosed in U.S. Pat. No. 6,196,998 B1 and comprises an outer cap made of a rigid thermoplastic material, consisting of a proximal sleeve and a distal sleeve. The proximal sleeve is configured to be coupled with the collar, whereas the distal sleeve is configured for engagement with the resilient closure. Between the proximal and distal end, frangible portions are provided that serve as tamper evidence means and prevent a rotation of the distal end relative to the proximal end. As the proximal end is coupled with the collar of the syringe, it is difficult to couple the needle assembly with the collar after breaking the frangible portions for removal of the distal end of the outer cap.

US 2013/0338603 A1 discloses a syringe having a closure including a closure cap that closes off the needle attachment piece, forming a seal, and a securing cap. The securing cap surrounds the closure cap and is attached to the needle attachment piece by way of a holding ring. The securing cap and the closure cap are configured in one piece, which can make manufacturing difficult. A related syringe is disclosed in US 2010/0168678 A1.

A further syringe caps is disclosed in US 2013/0237911 A1, which has, however, a complicated structure.

SUMMARY OF THE INVENTION

It is an object of the present invention to provide an enhanced syringe tip cap of a simple configuration that offers tamper evidence means, is configured to reliably hold a resilient closure at a syringe tip for sealing the syringe tip and can be produced easily and at lost costs.

It is a further object of the present invention to provide an enhanced syringe tip cap that can be removed from the syringe tip easily and in a convenient, intuitive manner.

It is a further object of the present invention to provide an enhanced method of sealing a syringe using such a syringe tip cap and a syringe comprising such a syringe tip cap.

According to a first aspect of the present invention there is provided a syringe tip cap for retaining a resilient closure at a distal end of a syringe tip on which a collar for coupling with a syringe needle is mounted, comprising: a rigid outer cap having a distal cap member and a proximal sleeve member, wherein an annular first breaking line is formed between the distal cap member and the proximal sleeve member; and tamper indicator means comprising frangible portions which are broken when the annular first breaking line is broken; wherein the distal cap member is cup-shaped for accommodating and covering a distal end of the resilient closure, and configured for pressing the resilient closure toward the syringe tip; and the proximal sleeve member comprises a distal end and a proximal end configured to be coupled with the collar, for coupling the syringe tip cap with the distal end of the syringe tip; wherein the proximal sleeve member comprises a second breaking line extending between the distal end and the proximal end of the proximal sleeve member; the distal cap member and the proximal sleeve member of the rigid outer cap are connected with each other via an axial coupling strip, which bridges and disrupts the annular first breaking line; and the frangible portions of the tamper indicator means are weaker than the coupling strip, so that the distal cap member and the proximal sleeve member of the rigid outer cap can be partially separated by breaking the annular first breaking line and the coupling strip serves as a hinge for pivotally coupling the distal cap member and the proximal sleeve member of the rigid outer cap after the annular first breaking line has been broken.

The syringe tip cap according to the present invention serves for retaining a resilient closure at a distal end of a syringe tip on which a collar for coupling with a syringe needle is mounted. An annular first breaking line is formed between the distal cap member and the proximal sleeve member, which extends preferably perpendicular to an axial direction of the syringe tip cap/syringe barrel, but may also extend slanted at small angle relative to a direction perpendicular to the axial direction of the syringe tip cap/syringe barrel. The distal cap member is cup-shaped and configured for accommodating and covering a distal end of the resilient closure, and configured for pressing the resilient closure toward the syringe tip. The proximal sleeve member is formed as a tubular sleeve that can be fitted over the syringe tip and comprises a distal end and a proximal end configured to be coupled with the collar, for coupling the syringe tip cap with the distal end of the syringe tip. In the proximal sleeve member, a second breaking line is formed extending between the distal end and the proximal end of the proximal sleeve member.

By breaking the frangible portions of the annular first breaking line the distal cap member and the proximal sleeve member of the rigid outer cap can be partially separated to provide access to the upper surface of the resilient closure, which may be sufficient to couple the needle assembly with the collar and puncture the resilient closure for administering the medication. The first breaking line is broken preferably by pushing the distal cap member obliquely toward a distal end of the tip cap and pivoting it about the coupling strip. The coupling strip serves thus as a hinge for pivotally coupling the distal cap member and the proximal sleeve member of the rigid outer cap after the annular first breaking line has been broken.

This procedure for breaking the first breaking line and opening the tip cap for providing access to the resilient closure is convenient for a user and may be performed with one finger only, preferably with a thumb, while holding the syringe barrel with the other fingers of the same hand.

The second breaking line extends substantially perpendicularly to the annular first breaking line, i.e. it may extend in axial direction or extend under a relatively small acute angle relative to the axial direction. Once the first breaking line is broken, the distal cap member may thus be used as a handle or tab to further pull-down the distal cap member in proximal direction. As this pulling direction (nearly) coincides with the direction of the second breaking line, the second breaking line can be broken easily. The syringe tip cap may thus be removed from the syringe tip easily and in a convenient, intuitive manner. The second breaking line preferably extends from the annular first breaking line until the proximal and of the proximal sleeve member, so that the proximal sleeve member may be easily torn-off until the proximal end of the sleeve member. According to a further embodiment, the second breaking line stops before reaching the proximal end of the proximal sleeve member so that, if the second breaking line is broken completely by breaking its frangible portions, the annular proximal end still remains to hold the proximal sleeve member on the syringe barrel, until also this annular proximal end is broken to tear-off the proximal sleeve member completely from the syringe barrel.

According to a further embodiment, a film hinge or thinner region extending perpendicular to the axial direction of the syringe tip cap is formed in the middle of the coupling strip, just in the center of the annular first breaking line. Thus, the distal cap member may be pivoted precisely about this film hinge at an early stage of opening the syringe tip cap already, for breaking the frangible portions of the annular first breaking line precisely and in a controllable, intuitive manner.

According to a further embodiment, the second breaking line formed in the proximal sleeve member is followed by a first slot, which is formed in the distal cap member and forms a first edge of the axial coupling strip. Thus, by continuing pulling the distal cap member toward the proximal end of the syringe barrel, the second breaking line can be broken as well, so that the whole tip cap may then be torn off from the syringe barrel to provide full access to the resilient closure.

According to a further embodiment, the axial coupling strip is further delimited by a second slot which is formed in the distal cap member and extends in parallel with the first slot, so that the axial coupling strip is rectangular and extends in axial direction of the syringe tip cap. Thus, a pulling tab is automatically formed when pivoting and pulling the distal cap member toward the proximal end of the syringe barrel, which may ease the breaking of the second breaking line.

According to a further embodiment, the second breaking line is slanted at an acute angle relative to the axial direction of the syringe tip cap, wherein the second breaking line comprises frangible portions extending substantially perpendicular to the axial direction of the syringe tip cap. This acute angle may be of the order of a few degrees only, which may be sufficient to generate forces in a direction perpendicular to the axial direction of the syringe barrel when pulling the distal cap member toward the proximal end of the syringe barrel. These force components act in the same direction as the direction of the frangible portions of the second breaking line and thus help to break the second breaking line more easily and in a controlled manner.

According to a further embodiment, the proximal sleeve member of the syringe tip cap further comprises a third breaking line, which is preferably also formed by frangible portions that are broken if the third breaking line is broken. Preferably, the second and third breaking lines extend in parallel with each other so that the second and third breaking lines can be broken simultaneously to thereby form a rectangular pulling tab that can be used to more efficiently break the frangible portions of the second and third breaking lines when the distal cap member is pulled-down.

According to a further embodiment, the distal cap member comprises a step formed at a side wall of the distal cap member opposite to a position wherein the coupling strip bridges the second breaking line. This step precisely guides the movement of a user when pushing the distal cap member for breaking the annular first breaking line. Thus, already when pushing the step obliquely upward toward the distal end of the tip cap, the coupling strip serves as a hinge for pivotally coupling the distal cap member with the proximal sleeve member, which eases the breaking of the frangible portions of the annular first breaking line.

According to a further embodiment, the step is formed by a vertical side wall extending in the axial direction of the syringe tip cap and a slanted surface, which is slanted relative to a bottom of the distal cap member, so that by pushing the vertical side wall obliquely upward the distal cap member can be pushed from the proximal sleeve member of the rigid outer cap to thereby break the annular first breaking line and partially separate the proximal sleeve member from the rigid outer cap. The vertical side wall significantly eases the pushing of the distal cap member for breaking the annular first breaking line and thus renders the handling of the syringe tip cap intuitive and user-friendly.

According to a further embodiment, a pressing member protrudes from an inner surface of the distal cap member of the rigid outer cap at a center thereof, for pressing the resilient closure toward the syringe tip. This pressing member preferably protrudes from the inner surface over such a distance that the resilient closure can remain seated on the syringe tip and is not sheared off when the distal cap member is pivoted about the coupling strip. By adjusting the axial length of the pressing member, the pressure exerted onto the resilient closure, when the syringe tip cap is mounted, can be adjusted precisely in accordance with individual specifications. The pressing member may comprise a cylindrical or hollow-cylindrical protrusion or a convexely-curved protrusion on the inner surface of the distal cap member at a center thereof. The pressing member may also comprises at least two concentric, hollow-cylindrical protrusions provided on the inner surface of the distal cap member at a center thereof, that may also have different heights.

According to a further embodiment, a transparent portion may be disposed in a side wall of the distal cap member so that a contact region between the pressing member and the resilient closure and/or an upper surface of the resilient closure is visible from outside the syringe tip cap.

According to a further embodiment, a plurality of locking protrusions is formed on an inner side wall of the proximal end of the proximal sleeve member, which are configured for coupling the syringe tip cap with the distal end of the syringe tip, e.g. for gripping behind an edge of the collar.

According to a further embodiment, the locking protrusion are formed at equiangular intervals along the inner side wall of the proximal end of the proximal sleeve member, said locking protrusions having slanted insertion surfaces so that the syringe tip cap can be pushed onto the syringe tip more easily.

According to a further embodiment, the diameter of a circle along which the plurality of locking protrusions is disposed is smaller than a maximum outer diameter of the distal end of the resilient closure to be accommodated in the cup-shaped distal cap member so that the resilient closure can be retained in axial direction inside the cup-shaped distal cap member by the plurality of locking protrusions. This eases the mounting of the resilient closure and of the syringe tip cap on the distal end of a syringe barrel. Particularly, the syringe tip cap together with the resilient closure accommodated therein simply may be pushed in axial direction on the distal end of the syringe barrel to thus mount the syringe tip cap and at the same time to precisely position the resilient closure on the syringe tip, for sealing the syringe tip.

According to a further embodiment, a plurality of ridges may be formed on an inner surface of the proximal sleeve member, wherein the ridges are disposed at equiangular intervals along the inner surface of the proximal sleeve member and enclose a circle having a diameter, which is substantially equal to an outer diameter of the collar.

According to a further embodiment, the tip cap further comprises a resilient closure, which is accommodated and axially retained in the cup-shaped distal cap member.

According to a further related aspect of the present invention there is also provided a syringe tip cap for retaining a resilient closure at a distal end of a syringe tip on which a collar for coupling with a syringe needle is mounted, comprising: a rigid outer cap having a distal cap member and a proximal sleeve member and configured to be coupled with the collar, for coupling the syringe tip cap with the distal end of the syringe tip; and tamper indicator means comprising frangible portions which are broken when the annular first breaking line is broken; wherein the distal cap member is cup-shaped for accommodating and covering a distal end of the resilient closure, an annular first breaking line is formed between the distal cap member and the proximal sleeve member of the rigid outer cap, the proximal sleeve member comprises a second breaking line extending between a distal end and a proximal end of the proximal sleeve member, the second breaking line extends under an acute angle or under an angle of 90 degrees relative to the first breaking line, the second breaking line runs into the first breaking line at a point of intersection, and the distal cap member and the proximal sleeve member of the rigid outer cap are connected with each other via an axial coupling strip, which bridges and disrupts the annular first breaking line at a position adjacent to the point of intersection.

When the first breaking line is broken, e.g. by tearing or pivoting the distal cap member, the second breaking line is not also automatically broken, because the second breaking line extends under an acute angle or under an angle of 90 degrees relative to the first breaking line. Because the coupling strip bridges the annular first breaking line, the distal cap member and the proximal sleeve member of the rigid outer cap are still connected with each other via an axial coupling strip even after breaking the first annular breaking line. For this purpose, the axial coupling is formed a little bit stronger than the frangible portions of the first breaking line. Because the second breaking line runs into the first breaking line at a point of intersection, which is adjacent to the axial coupling strip, the axial coupling strip may serve as a hinge for pivotally coupling the distal cap member and the proximal sleeve member of the rigid outer cap after the annular first breaking line has been broken. Thus, the distal cap member may be pivoted away from the resilient closure, thus enabling access to the upper surface of the resilient closure and a puncture area provided there. In this position, where the distal cap member is pivoted away from the resilient closure and the proximal cep member, the upper surface of the resilient closure can be disinfected, e.g. by applying a disinfectant on the upper surface of the resilient closure. Furthermore, in this position a needle can also be punctured through the puncture area for drug administration.

Furthermore, because the second breaking line runs into the first breaking line at the afore-mentioned point of intersection, which is adjacent to the axial coupling strip, the axial coupling strip can be used as well as a pulling strip for complete removal of the syringe tip cap from the distal end of the syringe. Namely, by pulling the coupling strip basically in axial direction of the syringe, the frangible portions of the second breaking line start breaking, until all frangible portions of the second breaking line are finally broken. This operation may be performed by a user with a single hand. Accordingly, the syringe tip cap can be removed from the syringe tip easily and in a convenient, intuitive manner.

A further unitary aspect of the present invention is directed to a method of sealing a syringe barrel for administering a liquid containing a pharmaceutical drug, said method comprising the steps of: providing the syringe barrel having a syringe tip at a distal end thereof on which a collar for coupling with a syringe needle is mounted; sealing the syringe tip with a resilient closure; providing a syringe tip cap as outlined in the following; and pushing the syringe tip cap in axial direction on the distal end of the syringe barrel until the proximal end of the syringe tip cap is coupled with the collar and the resilient closure is pressed on the distal end of the syringe tip, for sealing the syringe tip.

A further unitary aspect of the present invention is directed to a method of sealing a syringe for administering a liquid containing a pharmaceutical drug, said method comprising the steps of: providing the syringe barrel having a syringe tip at a distal end thereof on which a collar for coupling with a syringe needle is mounted; providing a syringe tip cap as outlined in the following, which accommodates and axially retains a resilient closure in the cup-shaped distal cap member; and pushing the syringe tip cap together with the resilient closure in axial direction on the distal end of the syringe barrel until the resilient closure seals the syringe tip, the proximal end of the syringe tip cap is coupled with the collar and the resilient closure is pressed on the distal end of the syringe tip, for sealing the syringe tip.

A further aspect of the present invention relates to a syringe, wherein a syringe tip cap as outlined in the following is mounted at the distal end of a syringe tip of the syringe barrel, which engages with the collar at the syringe tip and retains a resilient closure at the distal end of the syringe tip, for sealing the syringe tip.

BRIEF DESCRIPTION OF THE DRAWINGS

The invention will now be described by way of example and with reference to the accompanying drawings, from which further features, advantages and problems to be solved will be-come apparent. In the drawings:

FIGS. 2a and 2b show in a perspective front and rear view a syringe barrel with a luer collar and a resilient closure mounted on the syringe tip;

FIGS. 4a and 4b show in a perspective front and rear view the syringe barrel of FIGS. 2a and 2b with the syringe tip cap of the first embodiment of the present invention;

FIGS. 5a to 5c show in different perspective top views the condition of a syringe tip cap of the first embodiment of the present invention after breaking a first annular breaking line at a first stage of removing the syringe tip cap from the syringe barrel;

FIGS. 8a to 8c show in different perspective top views the condition of a syringe tip cap of the second embodiment of the present invention after breaking the second and third breaking lines at a second stage of removing the syringe tip cap from the syringe barrel.

In the drawings, the same reference numerals designate identical or substantially equivalent elements or groups of elements.

DETAILED DESCRIPTION OF THE PREFERRED EMBODIMENTS

Figure 1:
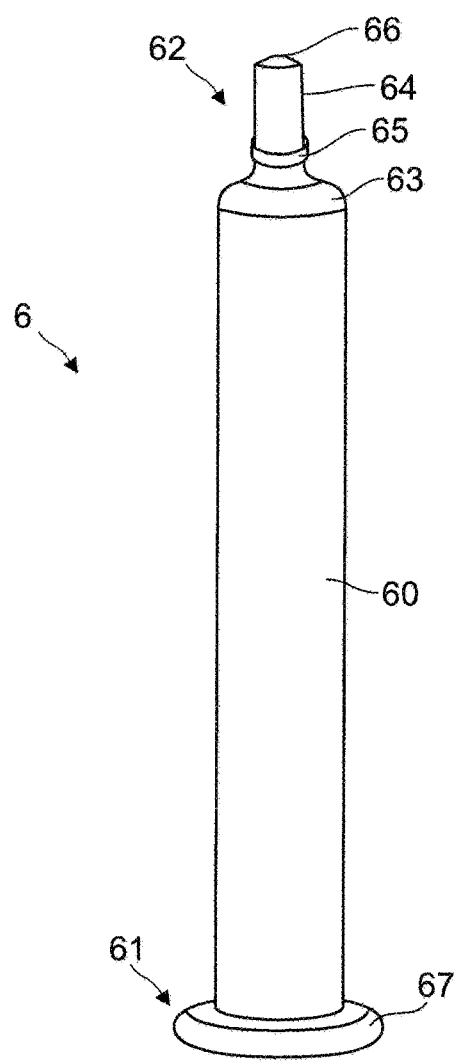
FIG. 1 shows a typical syringe barrel to be sealed by a resilient closure, for use with a syringe tip cap of the present invention.

As shown in FIG. 1, the syringe 6 includes a syringe barrel 60 which is formed from glass or plastic and is preferably transparent. The syringe barrel 60 includes a proximal end 61 having a flange 67, a distal end 62 and is a cylindrical body defining a substance receiving chamber which may be pre-filled with a selected dose of medication in either dry or liquid form, as well as other substances such as water or diluent for use in reconstituting a medicament. The distal end 62 of syringe barrel 60 includes a tip 64 having a passage extending therethrough and communicating with the substance receiving chamber. A plunger rod assembly (now shown) may extend into the proximal end 61 of the syringe barrel 60 via the filling opening 68, and include a stopper, which may slide in fluid-tight engagement inside the cylindrical wall. The syringe barrel 60 may be used with a standard needle assembly (not shown), which is generally known from the prior art.

The syringe barrel 60 generally does not have an integral collar for engaging the mounting hub of the needle assembly. As shown in FIGS. 2a and 2b, for this purpose a collar 4, particularly a luer collar, is mounted to the syringe tip 64 at the distal end 62 of the syringe barrel 60. The collar 4 includes a generally cylindrical body 40, having locking members 43 at a proximal end 42 thereof, configured for engagement with the syringe tip 64, e.g. with a groove or ridge 64 (see FIG. 1) provided on the outer surface of the syringe tip 64.

The needle assembly may be maintained separate from the syringe barrel 60, and may be mounted to the syringe barrel 60 a short time prior to usage of syringe 6. In this way, the syringe barrel 60 may be pre-filled with medication, and stored in its pre-filled condition prior to mounting needle assembly 30 thereto. To prevent contamination or leakage of medication stored in syringe barrel 60, a resilient closure 5 shown in FIGS. 2a and 2b seals the syringe tip 64. The resilient closure 5 is preferably made of an elastomeric material and comprises a cylindrical body (not shown), which is inserted into the syringe tip 64 to seal it. The distal end of the resilient closure 5 is of cylindrical shape and of a larger diameter, which usually corresponds to the outer diameter of syringe barrel 60. On the upper surface 51 of the distal end 50 and annular protrusion 52 is formed that can be used by a pressing member to exert a controlled and uniformly spread pressure onto the resilient closure 5, for pressing the resilient closure 5 in a controlled manner on syringe tip 64.

In order to keep the resilient closure 5 in place, in a proper engagement with the syringe tip 64 and to prevent a contamination of the resilient closure 5 during storage, a tip cap assembly generally denoted by reference numeral 1 is provided on the syringe tip 64 of the syringe barrel 60, as generally shown in FIGS. 4a and 4b.

The tip cap 1 is generally cup-shaped and suited to fully accommodate at least the distal end 50 of the resilient closure 5, for preventing a contamination of the distal end 50. The tip cap 1 is made of a rigid or sufficiently stiff plastic material, preferably by plastic injection molding. The tip cap 1 generally is a tubular member and preferably has a closed upper surface 20 at a distal end thereof, for covering the entire distal end of closure 5. More specifically, the tip cap 1 consists of a distal cap member 2 and a proximal sleeve member 3 that are connected with each other via frangible, web-like portions 11 disposed along a first annular breaking line 10 formed between the distal cap member 2 and the proximal sleeve member 3. These frangible, web-like portions 11 serve as tamper indicator means, as outlined below in more detail.

Figure 3B:
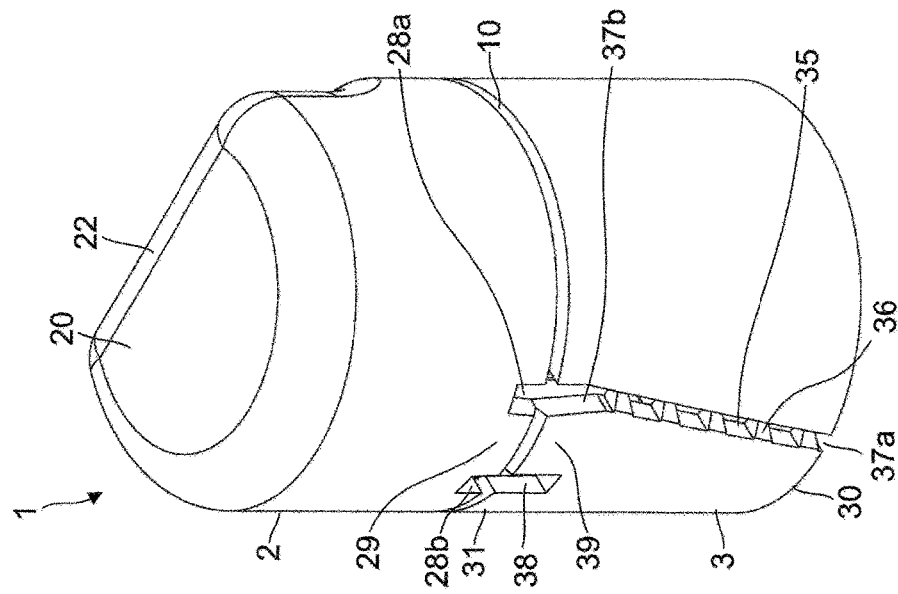
FIGS. 3a to 3c show a syringe tip cap according to a first embodiment of the present invention in two perspective side views and a perspective bottom view.
Figure 3A:
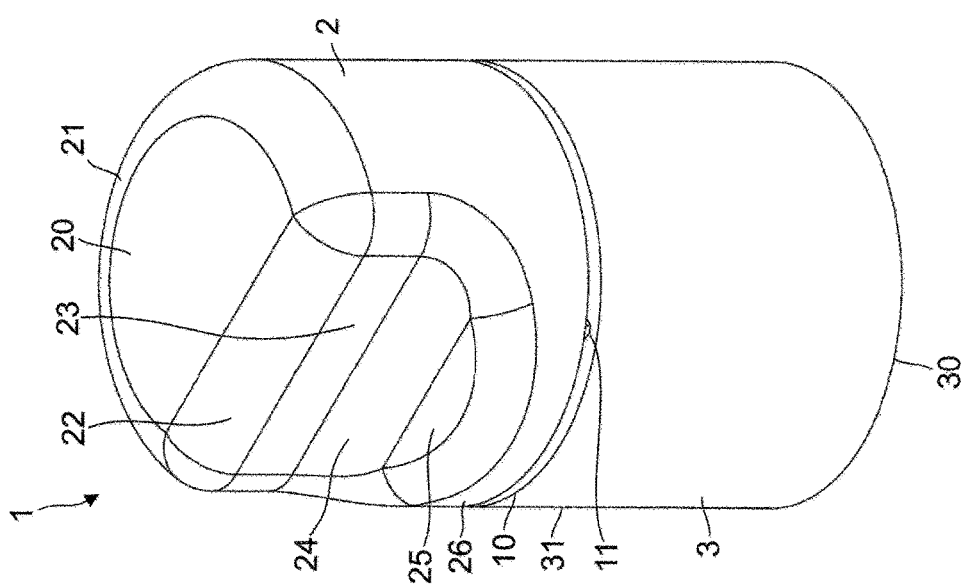
Figure 3C:
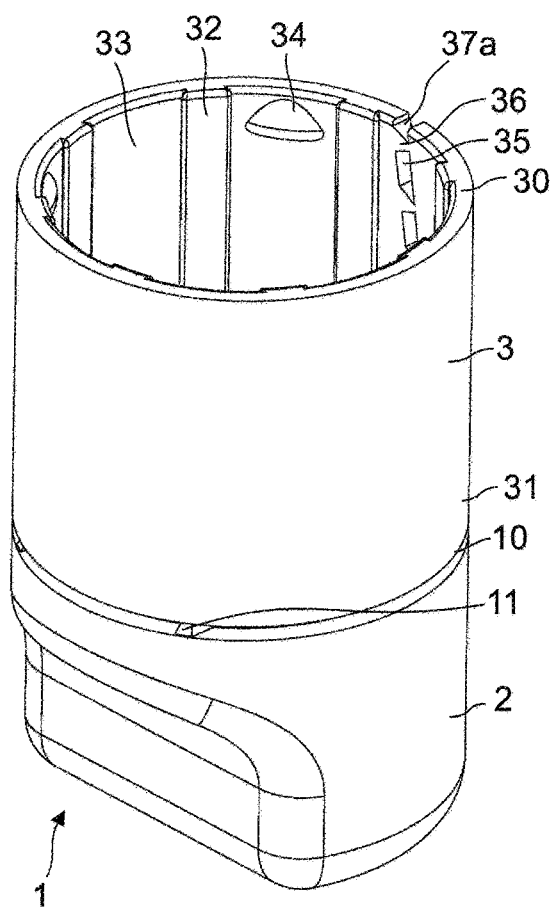

As shown in FIGS. 3a to 3c, the distal cap member 2 of the first embodiment of the present invention is generally cup-shaped, for fully accommodating the entire distal end of the resilient closure. When mounted on the distal end of syringe barrel 60, the annular first breaking line 10 is preferably below the position of the distal end 50 of closure 5, to provide full access to the closure 5 once the annular first breaking line 10 is broken and the distal cap member 2 is partially separated from the proximal sleeve member 3, as outlined below in more detail.

As shown in FIG. 3a, the distal cap member 2 is a cup-shaped cylindrical body having a closed upper surface 20, which is surrounded by a rounded upper rim 21 connecting with the circumferential side wall. The inner diameter of the distal cap member 2 is slightly larger than the outer diameter of the distal end 50 of closure 5 so that the closure 5 can be easily inserted and accommodated with radial play inside the distal cap member, when it is not compressed.

The annular first breaking line 10 is not fully circumferential, but disrupted by a coupling strip 29, which bridges the annular first breaking line 10 and couples the distal cap member 2 with the proximal sleeve member 3. The frangible portions 11 are weaker than the axial coupling strip 29. Hence, when the frangible portions 11 are broken by tilting the distal cap member 2 about coupling strip 29, the coupling strip 29 will continue coupling the distal cap member 2 with the proximal sleeve member 3. Thus, after breaking the annular first breaking line 10, the distal cap member 2 and the proximal sleeve member 3 will be separated only partially, but remain coupled with each other via coupling strip 29. The coupling strip 29 will thus serve as a hinge for pivotally coupling the distal cap member 2 and the proximal sleeve member 3 of the rigid outer cap 1 after the annular first breaking line 10 has been broken.

In order to ease a breaking of the annular first breaking line 10, a handling section is formed at the distal cap member 2 at a position opposite to the coupling strip 29 and slightly offset toward the distal end 20 of the distal cap member 2, so that a pivoting force will be exerted on the distal cap member 2 when operating the handling section, to ease a pivoting of the distal cap member 2 about the hinge formed by the coupling strip 29. More specifically, this handling section may be formed by a stepped portion on the outer surface of the distal cap member 2, as shown in FIG. 3a. This stepped portion is formed by a planar, vertical side wall 23, which extends from the distal end 20 toward the step 25, which is a substantially horizontal surface near the proximal end 26 of the distal cap member 2 and is connected with the vertical side wall 23 via a rounded horizontal edge 24. This stepped portion can be operated easily by a finger, preferably by a thumb, while holding the syringe barrel 60 with a hand. It is preferred to operate the tip cap 1 with only one hand, in which case the syringe barrel 60 will be held with the fingers of one hand, while the stepped portion will be pushed radially inward and toward the distal end 20 under an acute angle with respect to an axial middle line of the syringe barrel 60 so that a pivoting force will be exerted onto the distal cap member 2, which will finally break the frangible portions 11 of the first annular breaking line 10 and will finally result in the condition shown in FIGS. 5a to 5c.

As shown in FIG. 3b, the rectangular coupling strip 29 of the distal cap 2 is integrally connected with an opposite, rectangular coupling strip 39 of the proximal sleeve 3. More specifically, the coupling strips 29, 39 have a wedge-shaped profile, if viewed in a cross-sectional view, so that a film hinge is formed at the region where the two coupling strips 29, 39 are connected with each other. As shown in FIG. 3b, this film hinge is at the center of the first breaking line 10 and thus eases and guides the pivoting of the distal cap 2 about the proximal sleeve 3.

As shown in FIG. 3b, the coupling strip 29 is laterally delimited by two rectangular slots 28a, 28b and 37b, 38, respectively, which both extend in axial direction and are formed in the side wall of both the distal cap member 2 and the proximal sleeve member 3. More specifically, a first slot 28a is formed at a first side of the coupling strip 29 in the distal cap member 2 and a second slot 28b is formed at a second side of the coupling strip 29, in parallel with the first slot 28a. Directly opposite to these two slots 28a, 28b two corresponding slots 37b, 38 are formed at the distal end 31 of the proximal sleeve member 3. The first slot 37b communicates with a second breaking line 35 formed in the proximal sleeve member 3, extending between the distal end 31 and proximal end 30 thereof. Web-shaped second frangible portions 36 extend horizontally across the second breaking line 35. It is noted that the second breaking line 35 preferably extends under an acute angle with respect to the axial direction, preferably at an angle in the range between 45 degrees and 5 degrees, more preferably at an angle in the range between 30 degrees and 5 degrees and even more preferably at an angle in the range between 20 degrees and 10 degrees. It is also noted that the first slot 37b of the proximal sleeve member 3 extends in axial direction and can be considered as an extension of the first slot 28a of distal cap member 2.

Figure 4D:
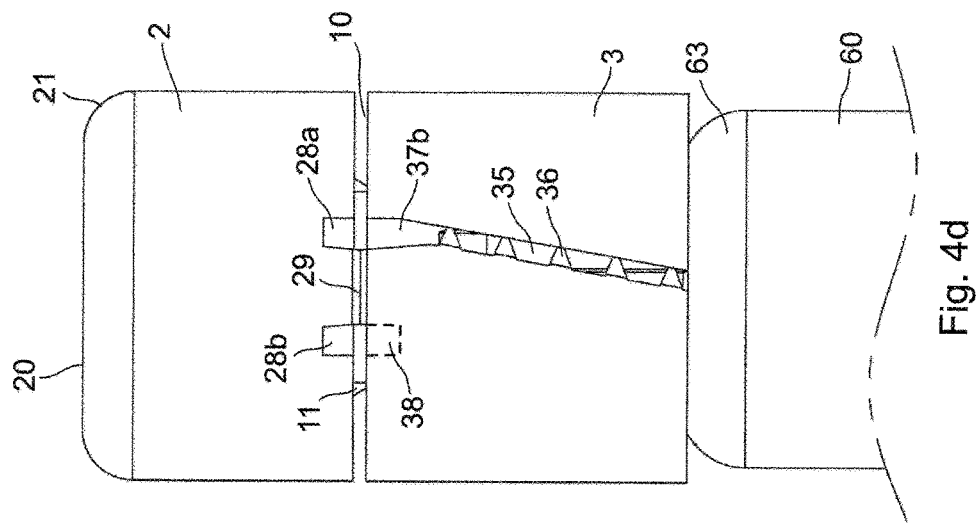
FIGS. 4c and 4d show in a front and rear view the syringe barrel of FIGS. 2a and 2b with the syringe tip cap of the first embodiment in an enlarged view.

As indicated by the dashed lines in FIG. 4d, the slot 38 in the proximal sleeve member 3 opposite to the axial slot 28b is optional and may also be omitted.

As shown in FIG. 3c, a plurality of locking protrusions 34 is formed on the inner surface of the proximal sleeve member 3 at a proximal end 30 thereof. The locking protrusions 34 are preferably disposed at equiangular distances to each other and protrude in radial direction inwards and each have an upper surface (not shown), which extends substantially perpendicularly to the side wall of proximal sleeve member 3, and a slanted insertion surface, which is directed toward the proximal end 30 for guiding the tip cap 1 when it is pushed over the distal end of the collar 4, as outlined below in more detail. After the tip cap 1 has been mounted on the syringe tip, the locking protrusions 34 grip behind the distal end of the collar 4, for coupling the tip cap 1 with the syringe 6 by latching or locking.

As shown in FIG. 3c, a plurality of axial ridges 32 is formed on the inner side wall 33 of proximal sleeve member 3 and disposed at a distance to the locking protrusions 34 and at equiangular intervals along the inner side wall 33 of proximal sleeve member 3. The ridges 32 enclose a circle having a diameter, which is substantially equal to an outer diameter of the collar 4 and/or the syringe 6, so that the collar 4 and/or the syringe 6 may abut with these ridges 32 in a mounted position. The ridges 32 serve for precisely centering the syringe in the tip cap 1 and for reducing friction when mounting the tip cap 1.

As shown in FIGS. 3b and 4b, the second breaking line 35 extends under an acute angle relative to the annular first breaking line 10. This acute angle may be in the range between 5 degrees and 45 degrees, more preferably in the range between 7.5 degrees and 30 degrees, even more preferably in the range between 10 degrees and 20 degrees. However, the angle of intersection between the second breaking line 35 and annular first breaking line 10 may also be 90 degrees or nearly 90 degrees. As shown in FIGS. 3b and 4b, the second breaking line 35 runs into the first breaking line 10 at a point of intersection, which is basically formed by the axial slots 37b and 28a. The axial coupling strip 29 bridges the first breaking line 10 at a position directly adjacent this point of intersection. Thus, once all frangible portions 11 of the first breaking line 10 are broken, the distal cap member 2 and the proximal sleeve member 3 remain to be connected with each other via the axial coupling strip 29, which can then be used as a pulling tab for breaking the second breaking line 35 by pulling the axial coupling strip 29 basically along the direction of the second breaking line 35, until finally all frangible portions 36 of the second breaking line 35 are broken and the syringe tip cap 1 can be removed from the syringe by unwinding the proximal sleeve member 1 from the collar at the distal end of the syringe.

In the following, two methods according to the present invention for mounting the tip cap 1 on the syringe tip and sealing a syringe are described with reference to FIGS. 1 to 3c. According to a first embodiment of the method, first the resilient closure 5 is put on the syringe tip 64. Afterwards, the tip cap 1 is pushed on the distal end 62 of the syringe barrel 60, until the slanted insertion surfaces of the locking protrusions 34 get in contact with the distal edge of the collar 4. Then, the tip cap 1 is further pushed onto the distal end of syringe barrel 60 so that the front ends of the locking protrusions 34 slide over the outer surface of collar 4, until the locking protrusions 34 grip behind the proximal end of collar 4 to thereby retain the tip cap 1 on syringe barrel 60. In this position, the distal end 20 of tip cap 1 may slightly compress the resilient closure 5 and press it on syringe tip 64 to seal the syringe tip 64 safely. For exerting a controlled pressure on the upper surface 51 of the resilient closure 5 and properly spread this pressure over the upper surface 51, a cylindrical protrusion 27 (see FIG. 5a and FIG. 7b) may be formed on the inner surface of the distal end 20 of the distal cap member 2, in which case the pressure exerted on the upper surface 51 of the resilient closure 5 may be controlled by the axial length of the cylindrical protrusion.

According to a second embodiment of the method, first the resilient closure 5 is inserted into the tip cap 1. Because the diameter of a circle along which the plurality of locking protrusions 34 is disposed on the inner side wall 33 of proximal sleeve member 3 is smaller than a maximum outer diameter of the distal end 50 of the resilient closure 5 the resilient closure 5 is retained in axial direction inside the cup-shaped distal cap member 2 by the plurality of locking protrusions 34. Afterwards, the syringe tip cap 1 together with the resilient closure 5 are pushed in axial direction on the distal end 62 of syringe barrel 60 until the slanted insertion surfaces of the locking protrusions 34 get in contact with the distal edge of the collar 4. Then, the tip cap 1 is further pushed onto the distal end of syringe barrel 60 in the same manner as outlined in the previous section, until the locking protrusions 34 grip behind the proximal end of collar 4 to thereby retain the tip cap 1 on syringe barrel 60.

Figure 4C:
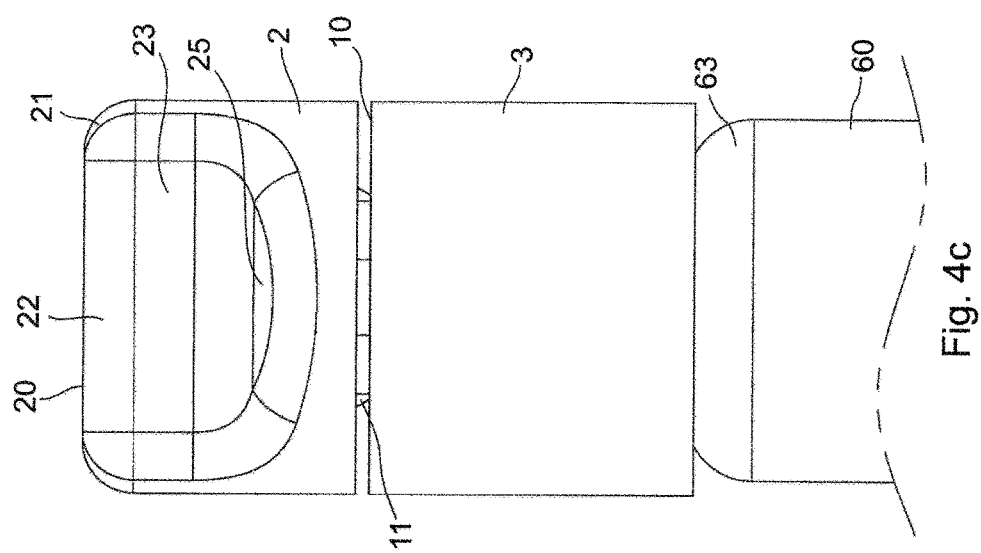

Because the resilient closure 5 is fully accommodated in the cup-shaped distal cap member 2, particles from outside cannot contaminate the upper surface 51 of the resilient closure 5. FIGS. 4a and 4b show the syringe 6 with the syringe tip cap 1 according to the present invention mounted at the distal end of syringe 6. FIGS. 4c and 4d show the syringe 6 with the syringe tip cap 1 according to the present invention mounted at the distal end of syringe 6 in an enlarged partial view.

For permitting a visible inspection of the contact area between the pressing member 27 (see FIG. 5a) on the inner surface of the distal end 20 and the upper surface 51 of the resilient closure 5, a transparent window (not shown) may be provided in a side wall of the distal cap member 2, particularly in the vertical side wall 23, so that the upper surface 51 of resilient closure 5 and/or a pressing member provided on the inner surface of the distal cap member 2 (cf. FIG. 7b) is visible from outside the syringe tip cap 1. This transparent window may be integrally formed with the tip cap 1, particularly by two-component plastic injection molding.

In the following, a process for giving access to the resilient closure 5 by partially separating the distal cap member 2 from the proximal sleeve member 3 and even for completely removing the tip cap 1 will be described with reference to FIGS. 4a to 6c.

At a first stage, a force directed obliquely toward the distal end of the syringe 6 is exerted on the distal cap member 2 by a user, particularly by pushing the vertical side wall 23 obliquely upward toward the distal end with the thumb of the user. This force will finally break the frangible portions 11 of the first annular breaking line 10 which hence serve as a tamper indicator means to provide such tamper evidence, as an integral and unmistakable evidence of tampering with the syringe barrel 60 and the medication therein. When the annular first breaking line 10 is broken, the distal cap member 2 is pivoted about the coupling strip 29, which is disposed opposite to the vertical side wall, until the condition shown in FIGS. 5a to 5c is reached. In this condition access is gained to the upper surface 51 of the resilient closure 5, which may be sufficient for administering the medication inside syringe barrel 60.

To gain full access to the entire resilient closure 5, the tip cap 1 may also be removed completely, which will be described with reference particularly to FIGS. 6a to 6c in the following.

For tearing off the tip cap 1 completely, the user may proceed further by gripping the distal end of syringe 6 with two fingers of one hand, particularly with the thumb and forefinger, and gripping the distal cap member 2 with two fingers of the other hand, particularly with the thumb and forefinger of the other hand. The user will continue tearing the distal cap member 2 into the same direction as previously pushing the distal cap member 2. In this condition, the distal cap member 2 will further pivot about the coupling strip 29 opposite to the vertical side wall 23. Finally, the distal cap member 2 is pivoted to such an extent about the coupling strip 29 that the coupling strip 29 basically serves as shackle to ease breaking the second breaking line 35 and completely tearing off the tip cap 1. This function is enhanced, because the two axial slots 37b and 38 that delimit the coupling strip 29 in the side wall of the proximal sleeve 3 enable pulling the coupling strip 29 a distance away from the side wall of the proximal sleeve member 3. Finally, the coupling strip 29 can be pulled in axial direction toward the proximal end of the proximal sleeve member 3, because the slot 37b serving as the distal end of the second breaking line 35 also extends in axial direction.

Figure 6C:
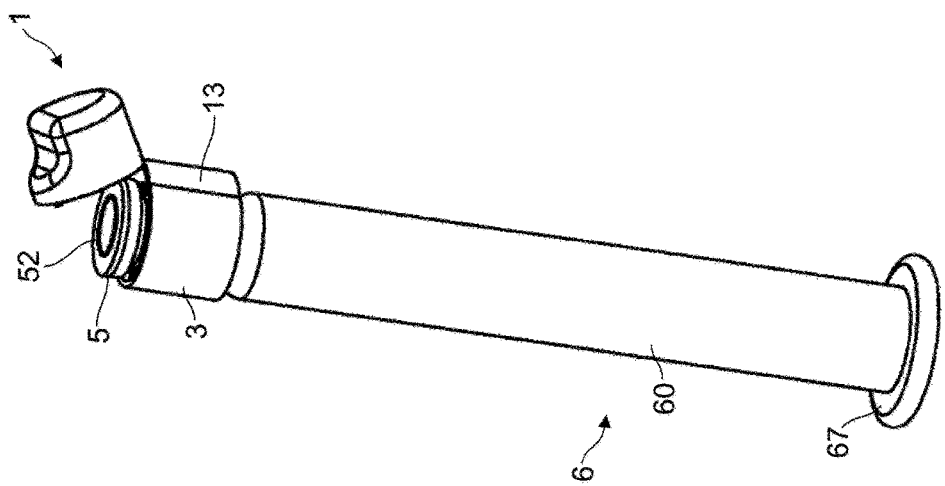
FIGS. 6a to 6c show in different perspective top views the condition of a syringe tip cap of the first embodiment of the present invention after breaking a second breaking line at a second stage of removing the syringe tip cap from the syringe barrel, subsequent to the first stage of FIGS. 5a to 5c.
Figure 6B:
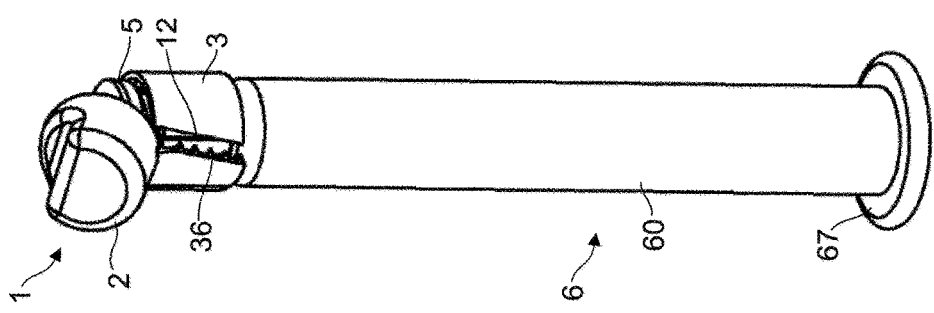
Figure 6A:
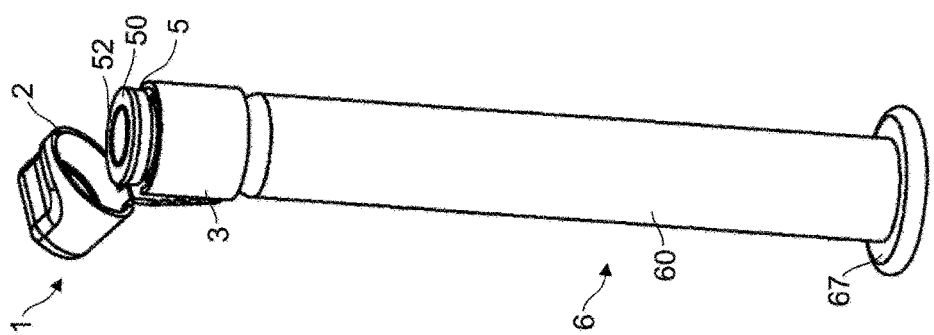

Then, the user continues pulling the coupling strip 29 toward the proximal end 30 of proximal sleeve member 3 so that one frangible portion 36 of the second breaking line 35 after the other is finally broken, as shown particularly in FIG. 6b, so that the proximal sleeve 3 can be unwound finally from the distal end of syringe 6, as shown particularly in FIG. 6c. That rim of the second breaking line 35 that is provided on the same side of the second breaking line 35 as the coupling strip 29 may thus serve as a pulling tab 13, as shown in FIG. 6c, for further pulling the proximal sleeve member and unwind the proximal sleeve member 3 from the distal end of the syringe 6. For this purpose, the user may grip the side of the proximal sleeve member 3 opposite to this pulling tab 13 and continue pulling the coupling strip 29, until all frangible portions 36 of the second breaking line 35 are broken and the proximal sleeve member 3 is finally unwound from the distal end of the syringe 6. Then, full access is gained to the resilient closure 5 on the distal end of syringe 6, for further handling, such as puncturing the closure 5 with a needle etc.

As will become apparent to a person skilled in the art, the above procedure for breaking the first breaking line, pivoting the distal cap member and finally complete removal of the syringe tip cap may of course also be performed with the fingers of a single hand.

To enable the above handling of the tip cap 1, the material of the tip cap 1 should be sufficiently flexible, particularly in the region of the coupling strip 29 bridging the annular first breaking line 10.

Figure 7B:
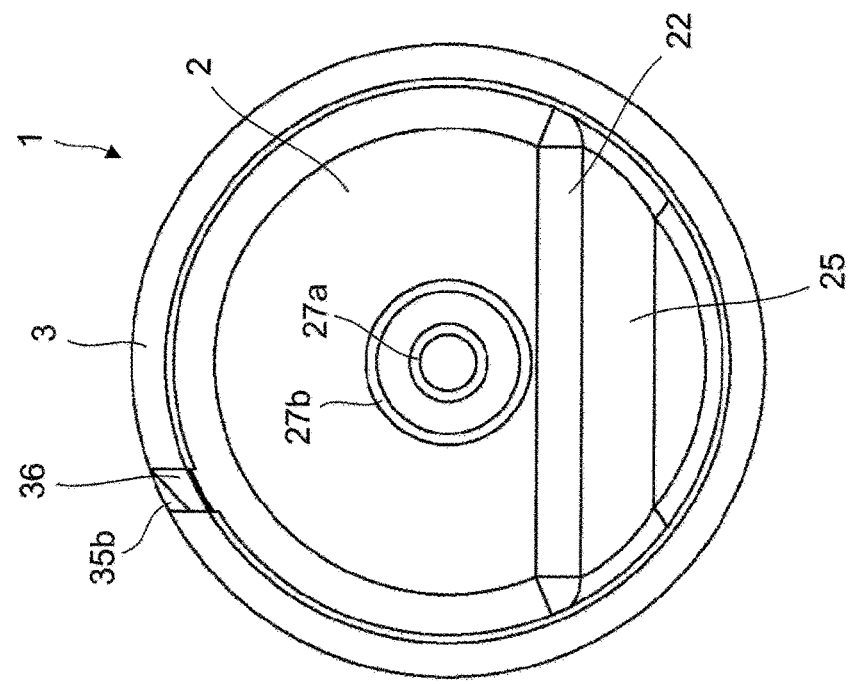
FIGS. 7a and 7b show a syringe tip cap according to a second embodiment of the present invention in a perspective side view and a bottom view.
Figure 7A:
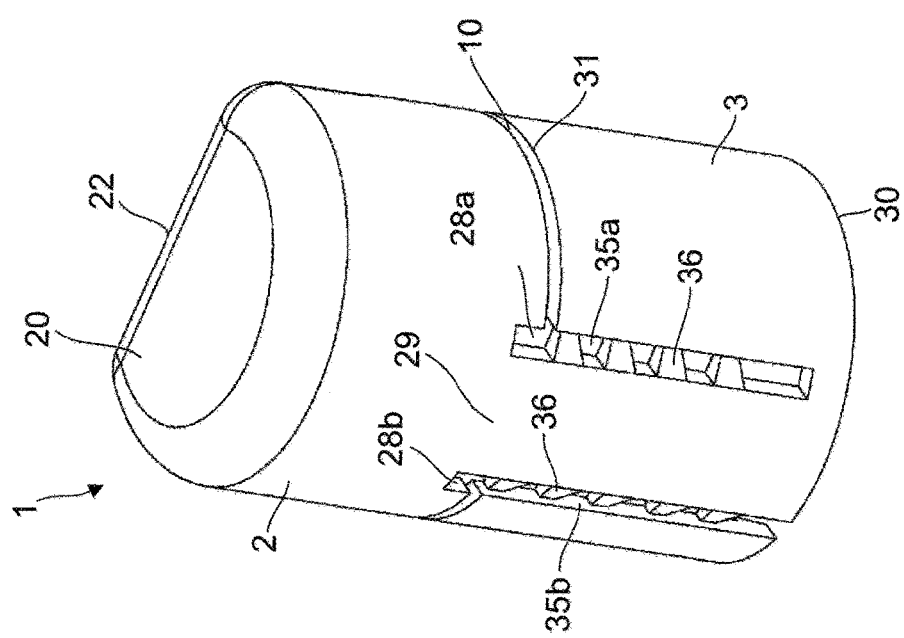

FIGS. 7a and 7b show a syringe tip cap 1 according to a second embodiment of the present invention. As shown in FIG. 7a, the second breaking line 35a extends basically in the axial direction of the syringe tip cap 1, but stops a short distance before reaching the proximal end 30 of the proximal sleeve member 3. According to this second embodiment, a third breaking line 35b extends in parallel with the second breaking line 35a, and may extend until the proximal end 30. Both the second and third breaking line 35a, 35b are formed by a linear groove which is bridged by web-shaped frangible portions 36 that are broken when breaking the second and third breaking line 35a, 35b. The second and third breaking line 35a, 35b is each followed by a respective short slot 28a, 28b formed in the distal cap member 2 at an opposite side of the annular first breaking line 10. As shown in FIG. 7a, the coupling strip 29 does not necessarily comprise a hinge as for the above first embodiment. Of course, such a hinge may be provided also in the second embodiment.

Once the annular first breaking line 10 is broken and the distal cap member 2 is pulled down toward the proximal end 30 the frangible portions 36 of the second and third breaking line 35a, 35b are broken, one after the other, so that a pulling tab of rectangular shape is formed between the second and third breaking line 35a, 35b, which acts as a lever for more efficiently break the second and third breaking line 35a, 35b when the distal cap member 2 is pulled down further toward the proximal end 30. FIGS. 8a to 8c show this pulling tab 13 at the second stage of removing the syringe tip cap 1 from the syringe barrel 60 by pulling down the distal cap member 2 toward the proximal end 30.

Figure 7C:
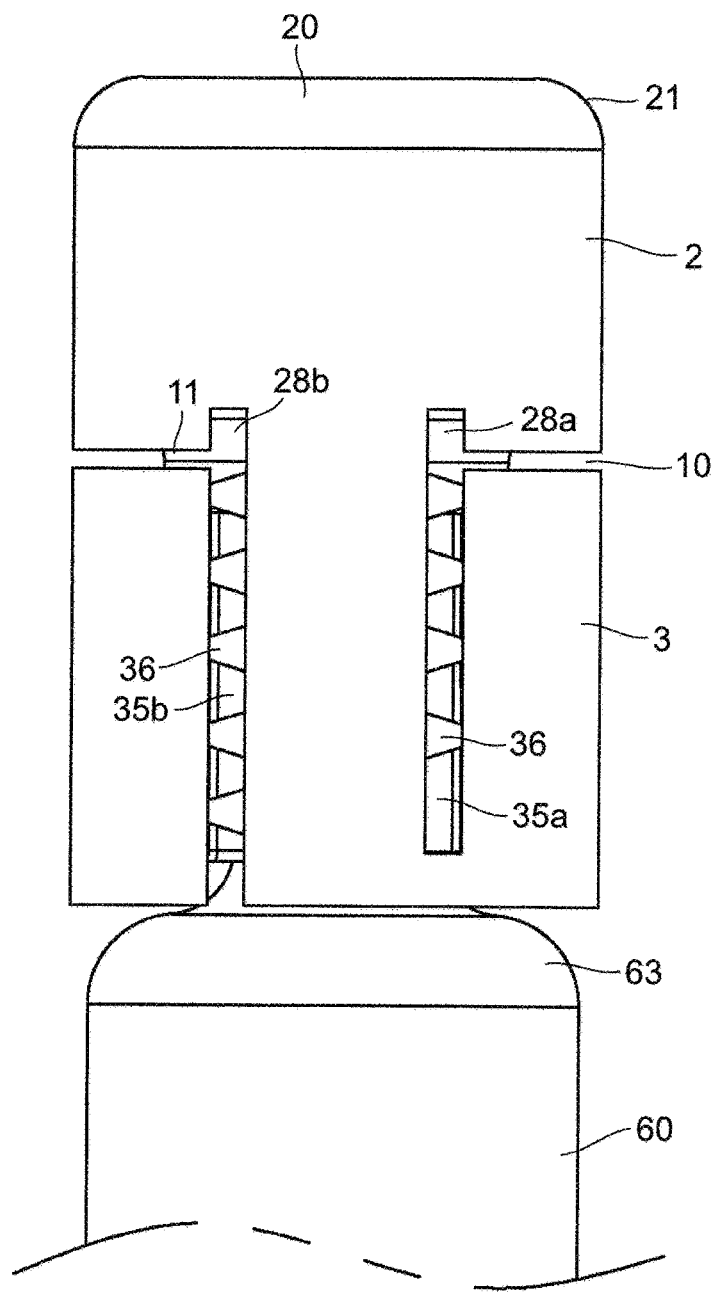
FIG. 7c shows in a side view the syringe barrel of FIGS. 2a and 2b with the syringe tip cap of the second embodiment in an enlarged view.

FIG. 7c shows the syringe tip cap 1 of the second embodiment in a rear side view, when mounted on the syringe barrel 60. Of course, the second and third breaking line 35a, 35b may also extend under an acute angle relative to the axial direction of the syringe tip cap 1, just as in the case of the first embodiment described above.

FIG. 7b shows a bottom view of the syringe tip cap 1 of the second embodiment. The pressing member formed in the bottom of the cap 1 consists of two concentric circular protrusions 27a, 27b, which may be of identical height, but which may also have different heights. The diameter of the outer pressing member 27b may be similar or slightly smaller than the diameter of protrusion 52 (see FIGS. 2a and 2b) of the resilient closure. The inner pressing member 27a is used to exert a controlled pressure at a central part of the upper surface 51 of resilient closure 5. The cooperation of the inner and outer pressing member 27a, 27b ensures a reliable sealing of the ejection opening 66 (see FIG. 1) of syringe barrel 60.

FIGS. 8a to 8c show in different perspective top views the condition of the syringe tip cap of the second embodiment of the present invention after breaking the second and third breaking lines at a second stage of removing the syringe tip cap from the syringe barrel. After breaking the first breaking line a pulling tab is formed between the second and third breaking line 35a, 35b, which is used to further break the frangible portions of the second and third breaking line 35a, 35b by pulling. After breaking all or nearly all frangible portions of the second and third breaking line 35a, 35b, a slight tilting of the distal cap member 2 relative to the syringe barrel is induced, because the third breaking line 35b is shorter in length than the second breaking line 35a. This tilting induces a circumferential motion component, which causes a widening of the gap between the edges of the second breaking line so that the syringe tip cap is finally unwound by a spiral-shaped movement.

While the preferred embodiments of the present invention have been described so as to enable one skilled in the art to practice the device of the present invention, it is to be understood that variations and modifications may be employed without departing from the concept and intent of the present invention as defined in the appended claims. Accordingly, the preceding description is intended to be exemplary and should not be used to limit the scope of the invention. The scope of the invention should be determined only by reference to the appended claims.

As will become apparent to a person skilled in the art when studying the above disclosure, the present invention also relates to the following embodiments of a syringe assembly:

Embodiment A

A syringe assembly, comprising:
  a syringe comprising a syringe barrel (6) having a substance receiving chamber extending along an axial direction, a syringe tip (64) projecting from a distal end of the syringe barrel (6) with a fluid passage extending through said syringe tip (64), and a collar (4) concentrically surrounding the syringe tip (64), for coupling with a syringe needle;
  a resilient closure (5) having a proximal end defining a tip engaging portion, which sealingly engages the syringe tip (64) to seal a substance contained in the substance receiving chamber of the syringe barrel (6); and a tamper evident syringe tip cap (1) mounted at the distal end of a syringe tip (64) and engaged with the collar (4), for retaining the resilient closure (5) at the distal end of the syringe tip (64) and sealing the syringe tip (64), said tamper evident syringe tip cap (1) comprising:

a rigid outer cap having a cup-shaped distal cap member (2), a proximal sleeve member (3) comprising a distal end (31) and a proximal end (30), an annular first breaking line (10), which extends perpendicularly to an axial direction of the tamper evident syringe tip cap (1), is formed between the distal cap member (2) and the proximal sleeve member (3) and comprises first frangible portions (11), and a second breaking line (35; 35a) extending between the distal end (31) and the proximal end (30) of the proximal sleeve member (3), wherein the proximal end (30) of the proximal sleeve member (3) is coupled with the collar (4) of the syringe barrel (6), and a distal end (50) of the resilient closure (5) is accommodated in the cup-shaped distal cap member (2) and protrudes beyond the distal end (31) of the proximal sleeve member (3); wherein the distal cap member (2) and the proximal sleeve member (3) are connected with each other via an axial coupling strip (29), which bridges and disrupts the annular first breaking line (10), and the first frangible portions (11) are weaker than the coupling strip (29), so that the distal cap member (2) and the proximal sleeve member (3) of the rigid outer cap can be partially separated by breaking the annular first breaking line (10) and the coupling strip (29) serves as a hinge for pivotally coupling the distal cap member (2) and the proximal sleeve member (3) of the rigid outer cap after the annular first breaking line (10) has been broken.

Embodiment B

The syringe assembly of Embodiment A, wherein
the second breaking line (35; 35a) communicates with a first slot (28a) formed in the distal cap member (2) and forming a first edge of the axial coupling strip (29), and
the axial coupling strip (29) is delimited by a second slot (28b) formed in the distal cap member (2) and extending in parallel with the first slot (28a), so that the axial coupling strip is rectangular and extends in axial direction of the tamper evident syringe tip cap (1).

Embodiment C

The syringe assembly of Embodiment B, wherein
the second breaking line (35; 35a) formed in the proximal sleeve member (3) extends at an acute angle relative to the axial direction of the tamper evident syringe tip cap (1).

Embodiment D

The syringe assembly of Embodiment B, wherein
a third breaking line (35b) is formed in the proximal sleeve member (3), said second breaking line (35a) and said third breaking line (35b) comprising frangible portions (36) which are broken when the second breaking line and third breaking line are broken, and said second breaking line and said third breaking line extending in parallel with each other.

Embodiment E

The syringe assembly of Embodiment A, wherein
a handling section is formed at a side wall of the distal cap member (2) opposite to a position where the axial coupling strip (29) bridges the annular first breaking line (10) and offset toward the distal end (20) of the distal cap member (2).

Embodiment F

The syringe assembly of Embodiment E, wherein
the handling section is formed as a stepped portion (25) in a side wall (23) of the distal cap member (2) extending in the axial direction of the tamper evident syringe tip cap (1) and including a surface extending radially inward perpendicular to or slanted relative to the axial direction of the tamper evident syringe tip cap (1), so that by pushing the vertical side wall (23) obliquely toward a distal end of the tamper evident syringe tip cap (1) the distal cap member (2) can be separated from the proximal sleeve member (3) of the rigid outer cap to thereby break the annular first breaking line (10) and partially separate the proximal sleeve member (3) from the rigid outer cap.

Embodiment G

The syringe assembly of Embodiment A, wherein
the syringe is a pre-filled syringe, which is pre-filled with a selected dose of a liquid containing a pharmaceutical drug, wherein a plunger is inserted into an open proximal end of the syringe barrel (6) opposite to the distal end of the syringe barrel (6).

| List of reference numerals | |
|---|---|
| 1 | syringe tip cap |
| 2 | distal cap member |
| 3 | proximal sleeve member |
| 4 | collar |
| 5 | resilient closure |
| 6 | syringe |
| 10 | annular first breaking line |
| 11 | frangible portion/coupling web |
| 12 | gap |
| 13 | pulling tab |
| 20 | upper surface/distal end |
| 21 | rounded upper rim |
| 22 | edge |
| 23 | vertical side wall |
| 24 | edge |
| 25 | step/slanted surface |
| 26 | proximal end |
| 27 | pressing member |
| 27a | outer pressing member |
| 27b | inner pressing member |
| 28a | first slot |
| 28b | second slot |

-continued

| List of reference numerals | |
|---|---|
| 29 | coupling strip |
| 30 | proximal end |
| 31 | distal end |
| 32 | inner ridge |
| 33 | inner side wall |
| 34 | locking protrusion |
| 35 | second breaking line |
| 35a | second breaking line |
| 35b | third breaking line |
| 36 | frangible portion/coupling web |
| 37a | proximal end of second breaking line |
| 37b | distal end of second breaking line |
| 38 | slot |
| 39 | coupling strip |
| 40 | cylindrical body |
| 41 | ridge |
| 42 | proximal end of collar 4 |
| 43 | locking member |
| 50 | distal end of resilient closure 5 |
| 51 | upper surface |
| 52 | protrusion |
| 53 | step |
| 60 | syringe barrel |
| 61 | proximal end |
| 62 | distal end |
| 63 | tip shoulder |
| 64 | syringe tip |
| 65 | groove |
| 66 | ejection opening |
| 67 | flange |
| 68 | filling opening |

What is claimed is:

1. A method of sealing a syringe barrel, comprising the steps of:
providing the syringe barrel (6), said syringe barrel (6) having a syringe tip (64) at a distal end thereof on which a collar (4) for coupling with a syringe needle is mounted;
sealing the syringe tip (64) with a resilient closure (5) so that the resilient closure (5) is seated on the syringe tip (64), said resilient closure (5) having a distal end (50);
providing a tamper evident syringe tip cap (1) comprising:
a rigid outer cap having a cup-shaped distal cap member (2), formed by a first side wall extending in an axial direction as a cylindrical body and having a closed upper surface (20), for accommodating and covering the distal end (50) of the resilient closure (5),
a proximal sleeve member (3) formed by a second side wall of the same outer diameter as the first side wall and extending in the axial direction, comprising a distal end (31) and a proximal end (30) and configured to be coupled with the collar (4) of the syringe barrel (60),
an annular first breaking line (10), which extends perpendicularly to an axial direction of the tamper evident syringe tip cap (1), is formed between the distal cap member (2) and the proximal sleeve member (3) and comprises first frangible portions (11), and
a second breaking line (35; 35a) extending between the distal end (31) and the proximal end (30) of the proximal sleeve member (3) in the second side wall and comprising second frangible portions (36), wherein
the distal cap member (2) and the proximal sleeve member (3) are connected with each other via an axial coupling strip (29), which bridges and disrupts the annular first breaking line (10),
the first frangible portions (11) and the second frangible portions (36) are weaker than the coupling strip (29), and
a handling section comprising a step (25), which comprises a surface extending radially inward from the first side wall and perpendicular to or slanted relative to the axial direction and a vertical side wall (23) extending in the axial direction, and is formed in the first side wall of the distal cap member (2) opposite to a position where the axial coupling strip (29) bridges the annular first breaking line (10); and
applying the tamper evident syringe tip cap (1) over the collar (4) and resilient closure (5), comprising:
pushing the tamper evident syringe tip cap (1) in the axial direction on the distal end of the syringe barrel (6)
until the proximal end (30) of the proximal sleeve member (3) is coupled with the collar (4), and
the distal end (50) of the resilient closure (5) is accommodated in the cup-shaped distal cap member (2) and protrudes beyond the distal end (31) of the proximal sleeve member (3) but not so far that it would inhibit pivoting the cup-shaped distal cap member (2) about the coupling strip (29), wherein
the distal cap member (2) is separated from the proximal sleeve member (3) of the rigid outer cap to break the first frangible portions (11) of the annular first breaking line (10) and partially separate the proximal sleeve member (3) from the rigid outer cap by pushing the vertical side wall (23) of the cup-shaped distal cap member (2) obliquely toward a distal end of the tamper evident syringe tip cap (1) and pivoting the cup-shaped distal cap member (2) about the coupling strip (29) while the resilient closure (5) remains seated on the syringe tip (64) to gain access to an upper surface (51) of the resilient closure (5), and
the second frangible portions (36) of the second breaking line (35; 35a) are broken to completely tear off the tamper evident syringe tip cap (1) from the distal end of the syringe barrel (6) by further pivoting the cup-shaped distal cap member (2) about the coupling strip (29) and pulling down the cup-shaped distal cap member (2) towards the proximal end (30) of the proximal sleeve member (3).

2. The method of sealing a syringe barrel as claimed in claim 1, wherein
the steps of sealing the syringe tip (64) with a resilient closure (5) and providing a tamper evident syringe tip cap (1) further comprise:
inserting the resilient closure (5) in the cup-shaped distal cap member (2) so that the resilient closure (5) is accommodated and axially retained in the cup-shaped distal cap member (2) before pushing the tamper evident syringe tip cap (1) in the axial direction on the distal end of the syringe barrel (6); and wherein
the step of pushing the tamper evident syringe tip cap (1) in the axial direction on the distal end of the syringe barrel (6) includes:
pushing the tamper evident syringe tip cap (1) together with the resilient closure (5) accommodated and axially retained in the cup-shaped distal cap member (2) in the axial direction on the distal end of the syringe barrel (6) until the proximal end (30) of the proximal sleeve member (3) is coupled with the collar (4), and the distal end (50) of the resilient closure (5) is accommodated in the cup-shaped distal cap member (2) and protrudes beyond the distal end (31) of the proximal sleeve member (3) but not so far that it would inhibit pivoting the cup-shaped distal cap member (2) about the coupling strip (29), for sealing the syringe tip.

3. The method of sealing a syringe barrel as claimed in claim 2, wherein the step of providing the tamper evident syringe tip cap (1) further comprises forming a plurality of locking protrusions (34) on an inner surface of the second side wall at the proximal end (30) of the proximal sleeve member (3), which are configured for gripping behind an edge of the collar (4) of the syringe barrel (6), wherein a diameter of a circle along which the plurality of locking protrusions (34) is disposed is smaller than a maximum outer diameter of the distal end (50) of the resilient closure (5) so that the resilient closure is retained in the axial direction inside the cup-shaped distal cap member (2) by the plurality of locking protrusions (34) after inserting the resilient closure (5) in the cup-shaped distal cap member (2).

4. The method of sealing a syringe barrel as claimed in claim 1, wherein the step of providing the tamper evident syringe tip cap (1) further comprises forming the second breaking line (35; 35a) in the second side wall of the proximal sleeve member (3) to communicate with a first slot (28a) formed in the first side wall of the cup-shaped distal cap member (2) and forming a first edge of the axial coupling strip (29), and delimiting the axial coupling strip (29) by a second slot (28b) formed in the cup-shaped distal cap member (2) and extending in parallel with the first slot (28a), so that the axial coupling strip is rectangular and extends in the axial direction of the tamper evident syringe tip cap (1).

5. The method of sealing a syringe barrel as claimed in claim 3, wherein the step of providing the tamper evident syringe tip cap (1) further comprises forming the second breaking line (35; 35a) in the second side wall of the proximal sleeve member (3) so as to extend at an acute angle relative to the axial direction of the tamper evident syringe tip cap (1).

6. The method of sealing a syringe barrel as claimed in claim 1, wherein the step of providing the tamper evident syringe tip cap (1) further comprises forming a third breaking line (35b) in the second side wall of the proximal sleeve member (3) comprising third frangible portions, wherein said second frangible portions (36) and said third frangible portions are broken when the second breaking line and the third breaking line are broken, and said second breaking line and said third breaking line extending in parallel with each other.

7. The method of sealing a syringe barrel as claimed in claim 1, wherein the step of providing the syringe barrel (6) comprises:

pre-filling the syringe barrel (6) with a selected dose of a liquid containing a pharmaceutical drug and inserting a plunger into an open proximal end of the syringe barrel (6) opposite to the distal end of the syringe barrel (6).

8. A method of filling a syringe, comprising the steps of:

providing a syringe barrel (6) having a syringe tip (64) at a distal end thereof on which a collar (4) for coupling with a syringe needle is mounted;

filling a chamber of the syringe barrel (6) with a liquid containing a pharmaceutical drug;

disposing a plunger within the chamber at an open proximal end thereof opposite to the distal end of the syringe barrel (6);

sealing the syringe tip (64) with a resilient closure (5) so that the resilient closure (5) is seated on the syringe tip (64), said resilient closure (5) having a distal end (50); and providing a tamper evident syringe tip cap (1) comprising:

a rigid outer cap having a cup-shaped distal cap member (2), formed by a first side wall extending in an axial direction as a cylindrical body and having a closed upper surface (20), for accommodating and covering the distal end (50) of the resilient closure (5), a proximal sleeve member (3) formed by a second side wall of the same outer diameter as the first side wall and extending in the axial direction, comprising a distal end (31) and a proximal end (30) and configured to be coupled with the collar (4) of the syringe barrel (60), an annular first breaking line (10), which extends perpendicularly to the axial direction of the tamper evident syringe tip cap (1), is formed between the distal cap member (2) and the proximal sleeve member (3) and comprises first frangible portions (11), and a second breaking line (35; 35a) extending between the distal end (31) and the proximal end (30) of the proximal sleeve member (3) in the second side wall and comprising second frangible portions (36), wherein the distal cap member (2) and the proximal sleeve member (3) are connected with each other via an axial coupling strip (29), which bridges and disrupts the annular first breaking line (10), the first frangible portions (11) and the second frangible portions (36) are weaker than the coupling strip (29), and a handling section comprising a step (25), which comprises a surface extending radially inward from the first side wall and perpendicular to or slanted relative to the axial direction and a vertical side wall (23) extending in the axial direction, and is formed in the first side wall of the distal cap member (2) opposite to a position where the axial coupling strip (29) bridges the annular first breaking line (10); and applying the tamper evident syringe tip cap (1) over the collar (4) and resilient closure (5) comprising:

pushing the tamper evident syringe tip cap (1) in the axial direction on the distal end of the syringe barrel (6) until the proximal end (30) of the proximal sleeve member (3) is coupled with the collar (4), and the distal end (50) of the resilient closure (5) is accommodated in the cup-shaped distal cap member (2) and protrudes beyond the distal end (31) of the proximal sleeve member (3) but not so far that it would inhibit pivoting the cup-shaped distal cap member (2) about the coupling strip (29), wherein the cup-shaped distal cap member (2) is separated from the proximal sleeve member (3) of the rigid outer cap to break the first frangible portions (11) of the annular first breaking line (10) and partially separate the proximal sleeve member (3) from the rigid outer cap by pushing the vertical side wall (23) of the cup-shaped distal cap member (2) obliquely toward a distal end of the tamper evident syringe tip cap (1) and pivoting the cup-shaped distal cap member (2) about the coupling strip (29) while the resilient closure (5) remains seated on the syringe tip (64) to gain access to an upper surface (51) of the resilient closure (5), and the second frangible portions (36) of the second breaking line (35; 35a) are broken to completely tear off the tamper evident syringe tip cap (1) from the distal end of the syringe barrel (6) by further pivoting the cup-shaped distal cap member (2) about the coupling strip (29) and pulling down the cup-shaped distal cap member (2) towards the proximal end (30) of the proximal sleeve member (3).

9. The method of filling a syringe as claimed in claim 8, wherein
the steps of sealing the syringe tip (64) with a resilient closure (5) and applying the tamper evident syringe tip cap (1) over the collar (4) and resilient closure (5) further comprise:
inserting the resilient closure (5) in the cup-shaped distal cap member (2) so that the resilient closure (5) is accommodated and axially retained in the cup-shaped distal cap member (2) before pushing the tamper evident syringe tip cap (1) in the axial direction on the distal end of the syringe barrel (6); and
pushing the tamper evident syringe tip cap (1) together with the resilient closure (5) accommodated and axially retained in the cup-shaped distal cap member (2) in the axial direction on the distal end of the syringe barrel (6) until the proximal end (30) of the proximal sleeve member (3) is coupled with the collar (4), and the distal end (50) of the resilient closure (5) is accommodated in the cup-shaped distal cap member (2) and protrudes beyond the distal end (31) of the proximal sleeve member (3) but not so far that it would inhibit pivoting the cup-shaped distal cap member (2) about the coupling strip (29), for sealing the syringe tip.

10. The method of filling a syringe in claim 9, wherein the step of providing the tamper evident syringe tip cap (1) further comprises
forming a plurality of locking protrusions (34) on an inner surface of the second side wall at the proximal end (30) of the proximal sleeve member (3), which are configured for gripping behind an edge of the collar (4) of the syringe barrel (6), wherein
a diameter of a circle along which the plurality of locking protrusions (34) is disposed is smaller than a maximum outer diameter of the distal end (50) of the resilient closure (5) so that the resilient closure is retained in the axial direction inside the cup-shaped distal cap member (2) by the plurality of locking protrusions (34) after inserting the resilient closure (5) in the cup-shaped distal cap member (2).

11. The method of filling a syringe as claimed in claim 8, wherein the step of providing the tamper evident syringe tip cap (1) further comprises
forming the second breaking line (35; 35a) in the second side wall of the proximal sleeve member (3) to communicate with a first slot (28a) formed in the first side wall of the cup-shaped distal cap member (2) and forming a first edge of the axial coupling strip (29), and delimiting the axial coupling strip (29) by a second slot (28b) formed in the distal cap member (2) and extending in parallel with the first slot (28a), so that the axial coupling strip is rectangular and extends in the axial direction of the tamper evident syringe tip cap (1).

12. The method of filling a syringe as claimed in claim 11, wherein the step of providing the tamper evident syringe tip cap (1) further comprises
forming the second breaking line (35; 35a) in the second side wall of the proximal sleeve member (3) so as to extend at an acute angle relative to the axial direction of the tamper evident syringe tip cap (1).

13. The method of filling a syringe as claimed in claim 8, wherein the step of providing the tamper evident syringe tip cap (1) further comprises
forming a third breaking line (35b) in the second side wall of the proximal sleeve member (3) comprising third frangible portions, wherein said second frangible portions (36) and said third frangible portions are broken when the second breaking line and the third breaking line are broken, and said second breaking line and said third breaking line extending in parallel with each other.

14. A method of sealing a syringe barrel, comprising the steps of:
providing the syringe barrel (6), said syringe barrel (6) having a syringe tip (64) at a distal end thereof on which a collar (4) for coupling with a syringe needle is mounted;
sealing the syringe tip (64) with a resilient closure (5) so that the resilient closure (5) is seated on the syringe tip (64), said resilient closure (5) having a distal end (50);
providing a tamper evident syringe tip cap (1) comprising:
a rigid outer cap having a cup-shaped distal cap member (2), formed by a first side wall extending in an axial direction as a cylindrical body and having a closed upper surface (20), for accommodating and covering the distal end (50) of the resilient closure (5),
a proximal sleeve member (3) formed by a second side wall of the same outer diameter as the first side wall as a cylindrical body and extending in the axial direction, comprising a distal end (31) and a proximal end (30) and configured to be coupled with the collar (4) of the syringe barrel (60),
an annular first breaking line (10), which extends perpendicularly to an axial direction of the tamper evident syringe tip cap (1), is formed between the distal cap member (2) and the proximal sleeve member (3) and comprises first frangible portions (11), and
a second breaking line (35; 35a) extending between the distal end (31) and the proximal end (30) of the proximal sleeve member (3) in the second side wall and comprising second frangible portions (36), wherein
the distal cap member (2) and the proximal sleeve member (3) are connected with each other via an axial coupling strip (29), which bridges and disrupts the annular first breaking line (10), and
the first frangible portions (11) and the second frangible portions (36) are weaker than the coupling strip (29); and
applying the tamper evident syringe tip cap (1) over the collar (4) and resilient closure (5), comprising:
pushing the tamper evident syringe tip cap (1) in the axial direction on the distal end of the syringe barrel (6)
until the proximal end (30) of the proximal sleeve member (3) is coupled with the collar (4), and
the distal end (50) of the resilient closure (5) is accommodated in the cup-shaped distal cap member (2) and protrudes beyond the distal end (31) of the proximal sleeve member (3) but not so far that it would inhibit pivoting the cup-shaped distal cap member (2) about the coupling strip (29), wherein
the distal cap member (2) is separated from the proximal sleeve member (3) of the rigid outer cap to break the first frangible portions (11) of the annular first breaking line (10) and partially separate the proximal sleeve member (3) from the rigid outer cap by pushing the cup-shaped distal cap member (2) at a position opposite to a position where the axial coupling strip (29) bridges the annular first breaking line (10) obliquely toward a distal end of the tamper evident syringe tip cap (1) and pivoting the cup-shaped distal cap member (2) about the coupling strip (29) while the resilient closure (5) remains seated on the syringe tip (64) to gain access to an upper surface (51) of the resilient closure (5), and the second frangible portions (36) of the second breaking line (35; 35*a*) are broken to completely tear off the tamper evident syringe tip cap (1) from the distal end of the syringe barrel (6) by further pivoting the cup-shaped distal cap member (2) about the coupling strip (29) and pulling down the cup-shaped distal cap member (2) towards the proximal end (30) of the proximal sleeve member (3).

\* \* \* \* \*